US012673030B2

(12) United States Patent
Kim et al.

(10) Patent No.: US 12,673,030 B2
(45) Date of Patent: Jul. 7, 2026

(54) PHARMACEUTICAL COMPOSITION FOR BURN TREATMENT COMPRISING TMD NANOSHEETS AS AN ACTIVE INGREDIENT

(71) Applicant: INDUSTRY-UNIVERSITY COOPERATION FOUNDATION HANYANG UNIVERSITY ERICA CAMPUS, Gyeonggi-do (KR)

(72) Inventors: Jong-Ho Kim, Gyeonggi-do (KR); Chul-Su Yang, Gyeonggi-do (KR); Da-Bin Yim, Gyeonggi-do (KR); Yoonhee So, Gyeonggi-do (KR)

(73) Assignee: INDUSTRY-UNIVERSITY COOPERATION FOUNDATION HANYANG UNIVERSITY ERICA CAMPUS, Gyeonggi-do (KR)

( * ) Notice: Subject to any disclaimer, the term of this patent is extended or adjusted under 35 U.S.C. 154(b) by 238 days.

(21) Appl. No.: 18/566,951

(22) PCT Filed: May 20, 2022

(86) PCT No.: PCT/KR2022/007207
§ 371 (c)(1),
(2) Date: Dec. 4, 2023

(87) PCT Pub. No.: WO2022/260307
PCT Pub. Date: Dec. 15, 2022

(65) Prior Publication Data

US 2024/0277626 A1 Aug. 22, 2024

(30) Foreign Application Priority Data

Jun. 10, 2021 (KR) ........................ 10-2021-0075489
Mar. 3, 2022 (KR) ........................ 10-2022-0027151

(51) Int. Cl.

| | |
|---|---|
| ***A61K 9/70*** | (2006.01) |
| ***A61K 33/04*** | (2006.01) |
| ***A61P 17/02*** | (2006.01) |
| ***C01G 41/00*** | (2006.01) |

(52) U.S. Cl.
CPC ................ *A61K 9/70* (2013.01); *A61K 33/04* (2013.01); *A61P 17/02* (2018.01); *C01G 41/00* (2013.01)

(58) Field of Classification Search
None
See application file for complete search history.

(56) References Cited

U.S. PATENT DOCUMENTS

2020/0215107 A1 7/2020 Chen

FOREIGN PATENT DOCUMENTS

| | | |
|---|---|---|
| CN | 105979975 | 1/2020 |
| KR | 10-1995-0703309 | 9/1995 |
| KR | 10-2012-0004076 | 1/2012 |
| KR | 10-2016-0049682 | 5/2016 |
| KR | 10-2020-0056694 | 5/2020 |

OTHER PUBLICATIONS

Huang et al. Silk fibroin-assisted exfoliation and functionalization of transition metal dichalcogenide nanosheets for antibacterial would dressings, 2017, The Royal Society of Chemistry, Nanoscale, vol. 9, pp. 17193-17198. (Year: 2017).*
Chen et al., Two-dimensional graphene analogues for biomedical applications, 2014, Chem. Soc. Rev., pp. 1-21. (Year: 2014).*
International Search Report mailed Sep. 15, 2022 for PCT/KR2022/007207.

* cited by examiner

*Primary Examiner* — Nannette Holloman

(57) ABSTRACT

Provided is a pharmaceutical composition for treating burns containing transition metal dichalcogenide (TMD) as an active ingredient.

16 Claims, 14 Drawing Sheets

PHARMACEUTICAL COMPOSITION FOR BURN TREATMENT COMPRISING TMD NANOSHEETS AS AN ACTIVE INGREDIENT

This application claims the priority of Korean Patent Application No. 10-2021-0075489, filed on Jun. 10, 2021, and 10-2022-0027151, filed on Mar. 3, 2022 in the KIPO (Korean Intellectual Property Office), the disclosure of which is incorporated herein entirely by reference. Further, this application is the National Stage application of International Application No. PCT/KR2022/007207, filed on May 20, 2022, which designates the United States and was published in Korean. Each of these applications is hereby incorporated by reference in their entirety into the present application.

TECHNICAL FIELD

The present invention relates to a pharmaceutical composition for treating burns, containing a TMD nanosheet as an active ingredient, and more particularly, to a pharmaceutical composition for treating burns, containing a TMD nanosheet as an active ingredient, the TMD nanosheet having an anti-inflammatory, apoptosis-prevention, and an antibacterial effect.

BACKGROUND ART

When the skin is burned, oxidative stress increases due to excessive generation of active oxygen species and active nitrogen species, and cell viability decreases through paths such as apoptosis, thereby slowing recovery of wounds.

Previously, burn treatments with antibacterial functions are used to prevent secondary infection of burn wounds, but they have strong cytotoxicity, which rather slow wound recovery.

In order to solve this problem, Korean Patent Publication No. 10-2012-0004076 and the like disclose a composition for treating burns using zinc and the like.

However, a novel pharmaceutical composition for treating burns, which can inhibit inflammation and prevent secondary infection caused by bacteria, and which does not actually have toxicity to normal cells, has not yet been disclosed.

DISCLOSURE OF THE INVENTION

Technical Problem

Accordingly, the problem to be solved by the present invention is to provide a novel pharmaceutical composition for treating burns, which has a high anti-inflammatory effect and low cytotoxicity against normal cells on the basis of an antioxidant effect.

Technical Solution

In order to solve the above problems, the present invention provides a pharmaceutical composition for treating burns comprising transition metal dichalcogenide (TMD) as an active ingredient.

In an embodiment of the present invention, the transition metal dichalcogenide (TMD) is a nanosheet.

The transition metal dichalcogenide may include at least one selected from the group consisting of $WS_2$, $MoS_2$, $MoSe_2$, and $WSe_2$.

In an embodiment of the present invention, the transition metal dichalcogenide (TMD) is a $WS_2$ nanosheet.

In an embodiment of the present invention, the $WS_2$ nanosheet has an absorption peak in a wavelength range of 600 to 700 nm.

In one embodiment of the invention, the $WS_2$ nanosheet is functionalized by PCL-b-PEG.

In one embodiment of the present invention, the pharmaceutical composition for treating burns has all of effects of preventing apoptosis, an anti-inflammatory effect, and an antibacterial effect through expression of an antibacterial peptide.

The present invention also provides a method for preparing a pharmaceutical composition for treating burns, comprising the steps of: adding transition metal dichalcogenide (TMD) to a polymer solution; ultrasonically treating the added solution; and obtaining a composition from a supernatant of the ultrasonically treated solution.

In one embodiment of the present invention, the polymer of the polymer solution is PCL-b-PEG.

In one embodiment of the present invention, the composition is the above-described pharmaceutical composition for treating burns.

Advantageous Effects

The pharmaceutical composition for TMD-based burn treatment according to the present invention has an anti-inflammatory, apoptosis-prevention, and an antibacterial effect based on the low toxic active oxygen species/nitrogen species scavenging activity for high normal cells.

BEST MODE FOR CARRYING OUT THE INVENTION

Hereinafter, a preferred embodiment of the present invention will be described in detail with reference to the accompanying drawings.

Before describing the present invention in detail, the terms or words used in the present specification should not be unconditionally construed as a general or dictionary meaning, and the inventors of the present invention may appropriately define and use the concepts of various terms in order to describe their invention in the best way.

Furthermore, it should be noted that these terms or words should be interpreted as meanings and concepts consistent with the technical idea of the present invention.

That is, the terms used in the present specification are merely used to describe the preferred embodiments of the present invention, and are not used to specifically limit the contents of the present invention.

It should be noted that these terms are defined in consideration of various possibilities of the present invention.

In addition, in the present specification, a singular expression may include a plurality of expressions unless the context clearly indicates a different meaning.

In addition, it should be noted that even when expressed in plural, it may include a singular meaning.

When a feature element is described as "including" another feature element throughout the specification, it may mean that any other feature element may be further included without excluding any other feature element unless there is a description of a particular opposite meaning.

In addition, in describing the present invention, a detailed description of a feature determined to unnecessarily obscure the gist of the present invention, for example, a known technology including the prior art, may be omitted.

In order to solve the above problems, the present invention utilizes a Transition Metal Dichalcogenide (TMD) material. The transition metal dichalcogenide has a structural formula of $MX_2$ (M=transition metal, X=chalcogen element), the structure of the transition metal dichalcogenide is a layered structure similar to graphene, the interval between layers is about 6-7 Å, and it is composed of a strong in-plane covalent bond and a weak out-of-plane van der Waals force. The transition metal of the transition metal dichalcogenide is tungsten (W), molybdenum (Mo), and the chalcogen element includes sulfur (S), selenide (Se), telluride (Te), and the like.

The present invention provides a novel pharmaceutical composition for treating burns based on a high active area as a two-dimensional material of the TMD material, and high scavenging activity for reactive oxygen species (ROS) and reactive nitrogen species (RNS).

Hereinafter, the present invention will be described in more detail according to the drawings and experimental examples. However, the scope of the present invention is not limited according to the following experimental examples.

Figure 1:
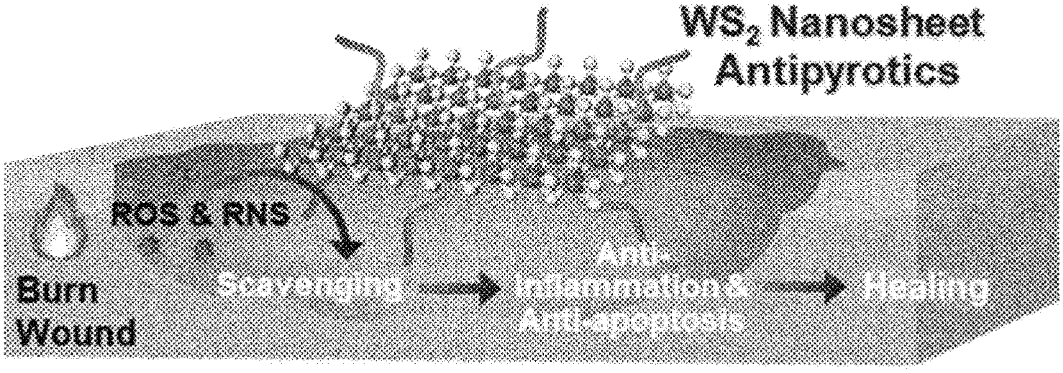
FIG. 1 is a schematic diagram illustrating an anti-inflammatory effect, an effect of preventing apoptosis, and an antibacterial effect of treating burns using TMD according to an embodiment of the present invention.

FIG. 1 is a schematic diagram illustrating an anti-inflammatory effect, an effect of preventing apoptosis, and an antibacterial effect of treating burns using TMD according to an embodiment of the present invention.

Referring to FIG. 1, the TMD nanosheet such as $WS_2$ according to the present invention scavenges reactive oxygen species (ROS) and reactive nitrogen species (RNS) to inhibit inflammatory reactions, apoptosis, and infection, and thus treats burns.

Example

2H-TMD Production 0.6 g of bulk $WS_2$ was added to 20 mL of PCL-b-PEG solution (2 mg/mL). The mixture was then sonicated for 1 hour (pulse-on for 6 sec, pulse-off for 2 sec), and the solution was centrifuged at 700×g for 1 hour to obtain a supernatant. The supernatant was centrifuged at 14, 500×g for 1 hour to produce a precipitate, and water was added to the precipitate under the same conditions and washed again by centrifugation. This precipitate was then dispersed with 8.5 mL of water and the solution was centrifuged at 2,000×g for 30 minutes to obtain TMD from the supernatant, the TMD obtained from this solution is referred to hereinafter as 2H-TMD, and in the present specification, the desired TMD material type may be used instead for the TMD. For example, when $WS_2$ is a TMD, 2H-$WS_2$ is a term referring to $WS_2$ manufactured according to the present embodiment.

1T-TMD Production

To 15 mL of n-butyllithium/hexane solution (1.6 M) in a round bottom flask, 1 g of bulk $WS_2$ powder was added at a temperature of 25° C. under $N_2$ conditions. After the reaction temperature was raised to 70° C., the mixture was stirred for 48 hours. The solution was centrifuged at 100×g for 10 minutes and the intermediate $WS_2$ was washed twice with hexane.

For the peeling, 80 mL of DI water in which 67 mg of PCL-b-PEG was dissolved was added to the Li-intercalated $WS_2$ powder and the resulting solution was sonicated using a bath sonicator for 1 hour. The exfoliated $WS_2$ nanosheets were centrifuged at 100×g for 15 minutes to obtain a supernatant. Then, the obtained supernatant was dialyzed for 5 days to remove lithium cations, and finally, the aqueous solution was centrifuged at 300×g for 30 minutes to obtain a supernatant including exfoliated 1T-$WS_2$ nanosheets. The TMD obtained herein is hereinafter referred to as 1T-TMD, and in the present specification, a desired TMD material type may be used instead for the TMD. For example, when $WS_2$ is a TMD, 1T-$WS_2$ is a term referring to $WS_2$ manufactured according to the present embodiment.

Experimental Example

TMD Analysis

Figure 2:
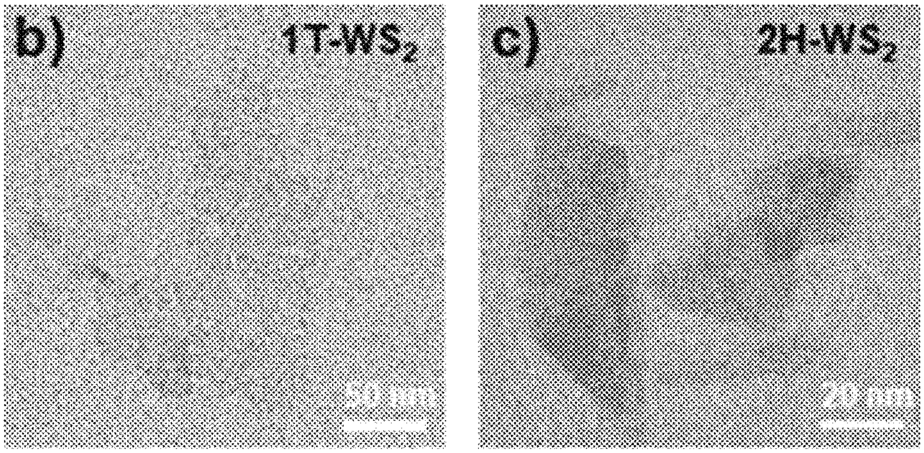
FIG. 2 is a TEM image of 2H-TMD and 1T-TMD according to an embodiment of the present invention.
Figure 3:
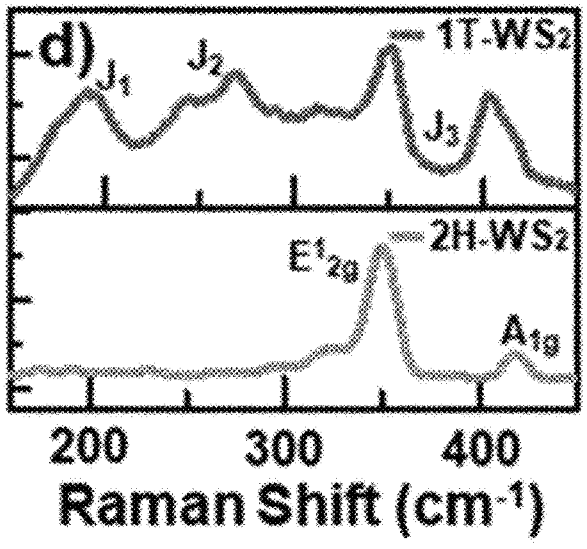
FIG. 3 is a Raman analysis result.
Figure 4:
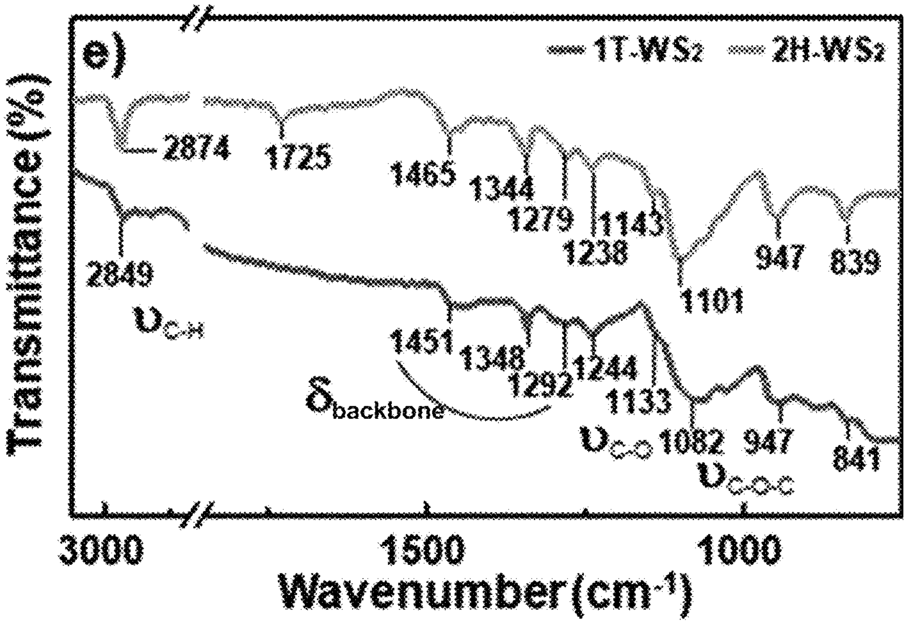
FIG. 4 is a FT-IR spectrum analysis result.
Figure 5:
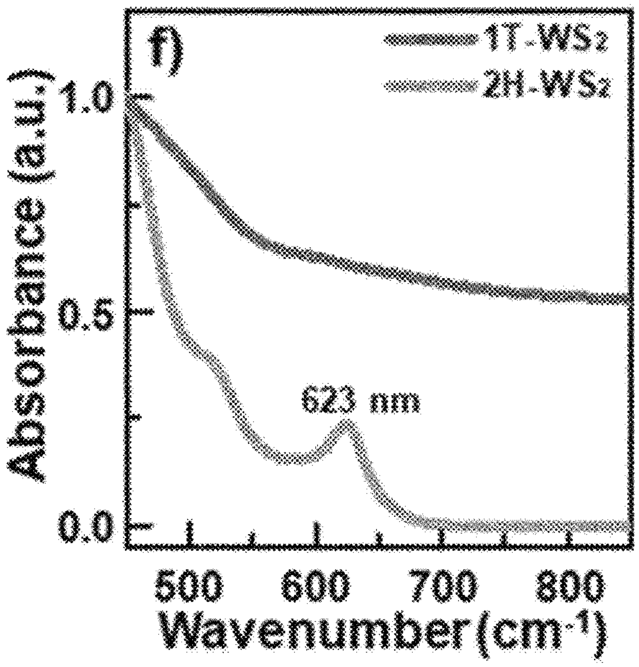
FIG. 5 is a UV-Vis spectrum analysis result.

FIG. 2 is a TEM image of 2H-TMD and 1T-TMD according to an embodiment of the present invention, FIG. 3 is a Raman analysis result, FIG. 4 is a FT-IR spectrum analysis result, and FIG. 5 is a UV-Vis spectrum analysis result.

Referring to FIGS. 2, 3, and 5, both 2H-TMD and 1T-TMD have distinct shapes and analysis peaks. In particular, referring to FIG. 3, Raman scattering of J1, J2, and J3 may be observed only on 1T, and referring to FIG. 5, it may be seen that the 1T-TMD exhibits an absorption peak in a wavelength range of 600 to 700 nm compared to 2H-TMD.

Figure 6:
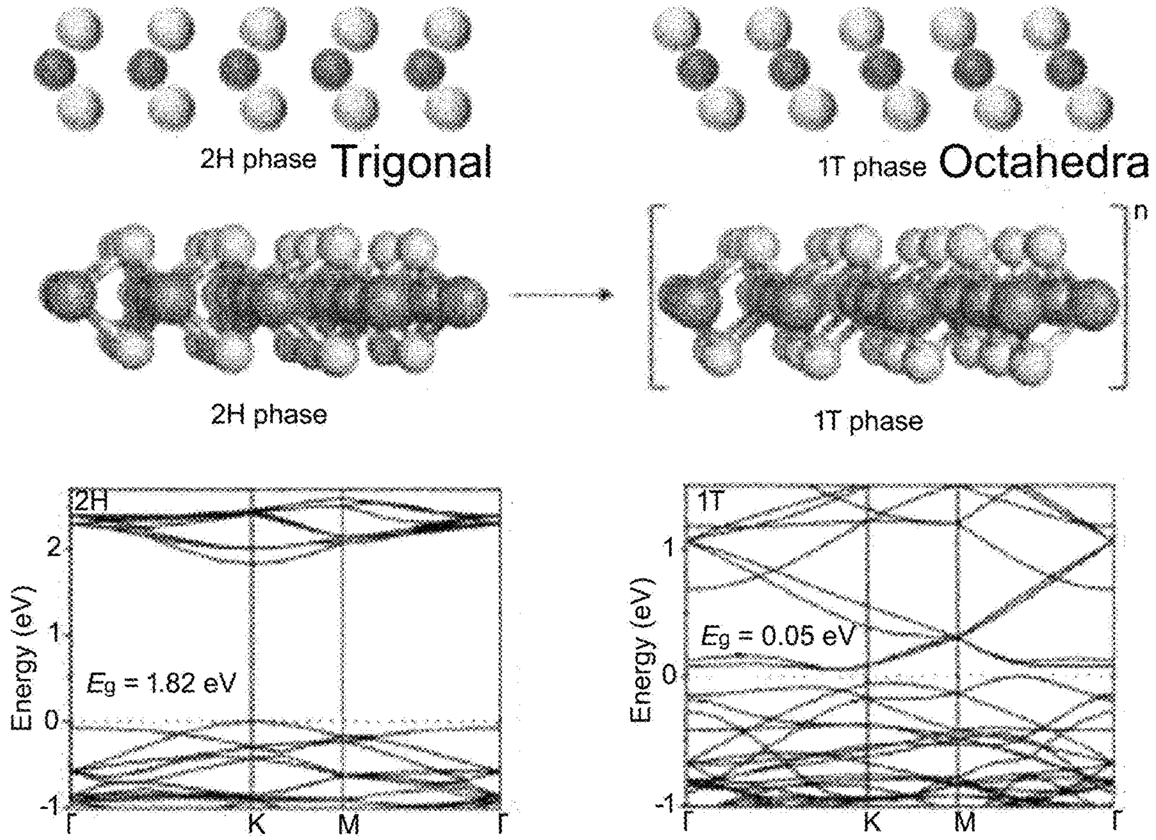
FIG. 6 illustrates structures of TMD nanosheets 2H-TMD and 1T-TMD manufactured according to an embodiment of the present invention, respectively.

FIG. 6 illustrates structures of TMD nanosheets 2H-TMD and 1T-TMD manufactured according to an embodiment of the present invention, respectively (Nat). Chem., 2015, 7, 45./J. Materiomics, 2018, 4, 329.).

Referring to FIG. 6, the electron arrangement is changed according to the TMD phase and the electrical, optical, and catalytic characteristics thereof are changed, and the 2H-$WS_2$ having a trigonal phase has a semiconductor characteristic, and the 1T-$WS_2$ having an octahedral phase has a metal characteristic.

Figure 7:
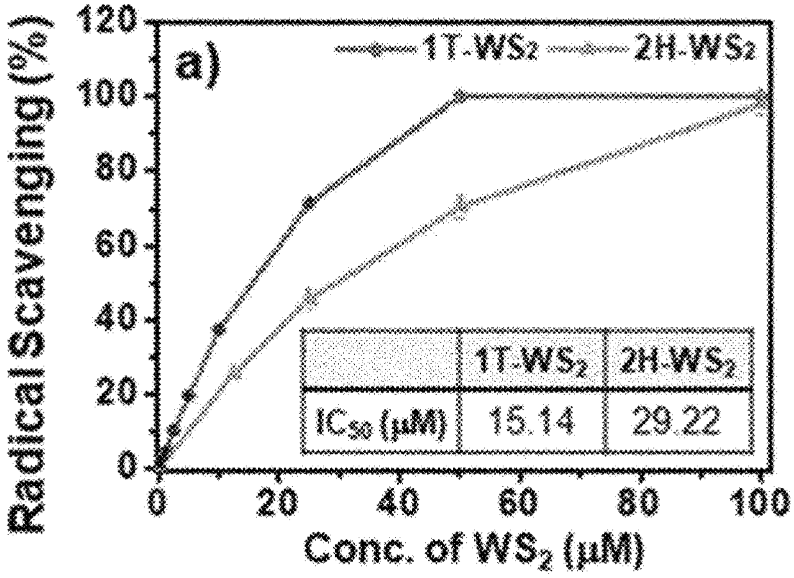
FIG. 7 is a result of testing ABTS radical scavenging ability 30 minutes after the addition of TMD nanosheets according to an embodiment of the present invention.

FIG. 7 illustrates experimental results of scavenging activity of ABTS radicals 30 minutes after adding TMD nanosheets to ABTS radicals according to an embodiment of the present invention.

Referring to FIG. 7, 1T-TMD (1T-$WS_2$) has better radical scavenging ability than 2H-TMD (2H-$WS_2$) with respect to the same concentration.

Figure 8:
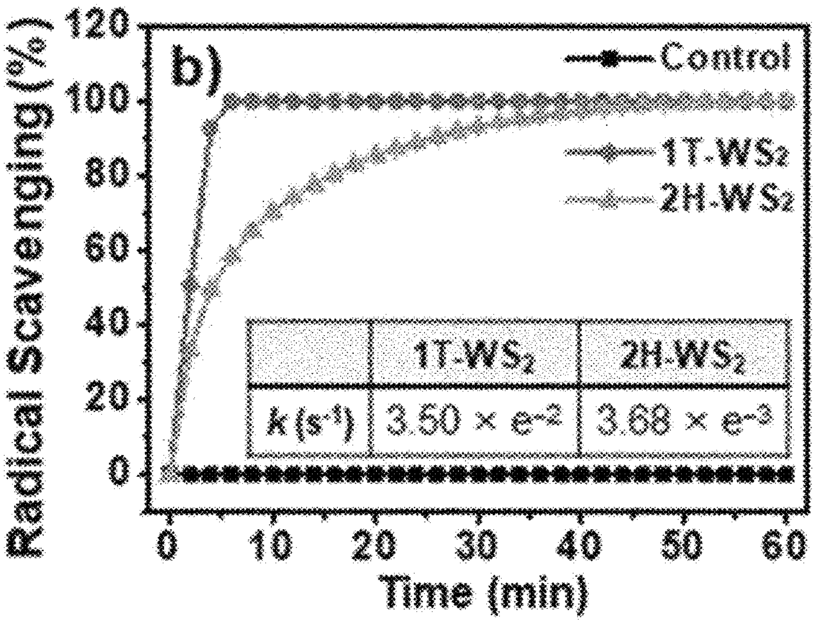
FIG. 8 shows the radical scavenging ability of 1T-$WS_2$ and 2H-$WS_2$ nanosheets (10 vg mL-1) with respect to ABTS radicals.
Figure 9:
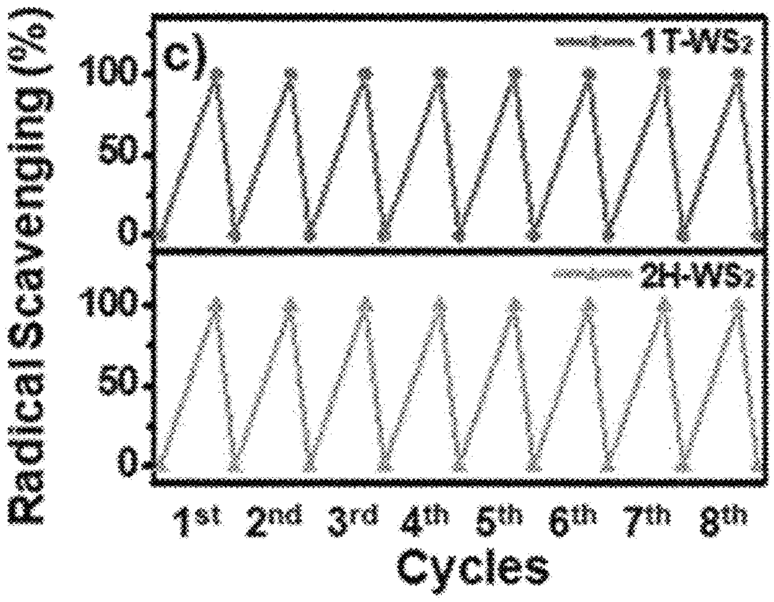
FIG. 9 shows the results of analyzing the sustainability thereof.

FIG. 8 shows the radical scavenging ability of 1T-$WS_2$ and 2H-$WS_2$ nanosheets (10 vg mL-1) with respect to ABTS radicals, and FIG. 9 shows the results of analyzing the sustainability thereof.

Referring to FIGS. 8 and 9, 1T-$WS_2$ reaches up to 100% of the scavenging rate earlier than 2H-$WS_2$, and both 1T-$WS_2$ and 2H-$WS_2$ can continuously scavenge radicals. This, in turn, suggests that the TMD-based treating burns agent according to the present invention may maintain an anti-inflammatory effect for a long time.

In-Vitro Cell Experiments

Figure 10:
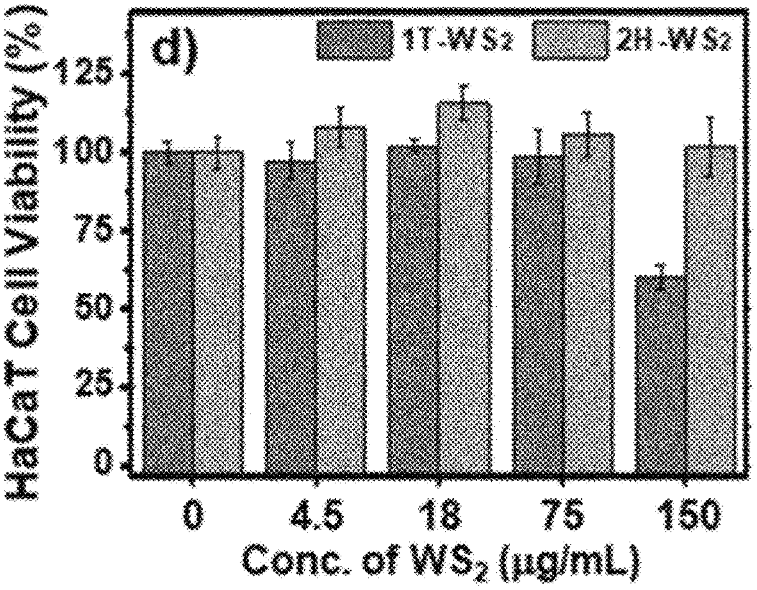
FIG. 10 shows the results of cytotoxicity evaluation on keratinocytes (HaCaT keratinocytes), which are normal cells.

FIG. 10 shows the results of cytotoxicity evaluation on keratinocytes (HaCaT keratinocytes), which are normal cells.

Referring to FIG. 10, 2H-$WS_2$ has relatively less toxicity to normal cells than 1T-$WS_2$. Particularly, when the concentration is increased, the low cytotoxic effect of 2H-$WS_2$ is more dramatic.

Figure 11:
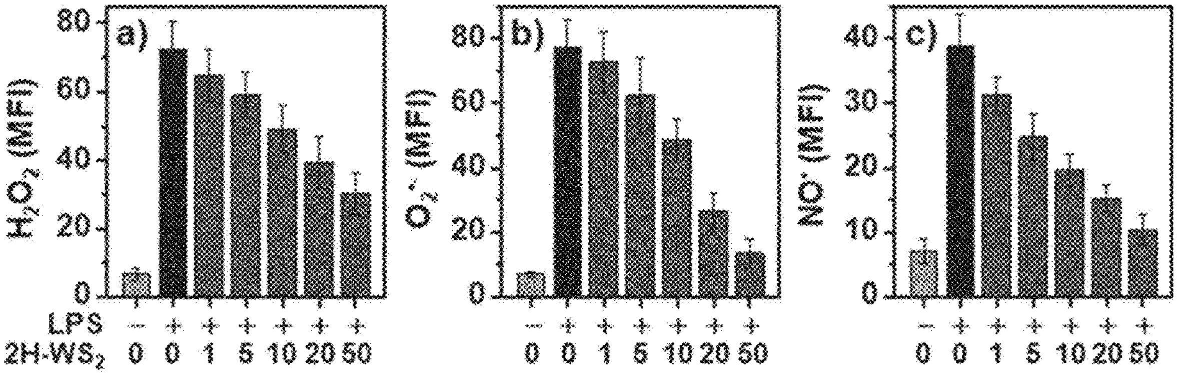
FIG. 11 is an experimental result on the oxidation stress suppression effect of 2H-$WS_2$ on hydrogen peroxide, superoxide, and nitrogen monoxide produced in HaCaT keratinocytes stimulated with lipopolysaccharide (LPS) from the left.

FIG. 11 is an experimental result on the oxidation stress suppression effect of 2H-$WS_2$ on hydrogen peroxide, superoxide, and nitrogen monoxide produced in HaCaT keratinocytes stimulated with lipopolysaccharide (LPS) from the left.

Referring to FIG. 11, it may be seen that oxidative stress of cells decreases as the use of 2H-$WS_2$ and its concentration increase.

Figure 12:
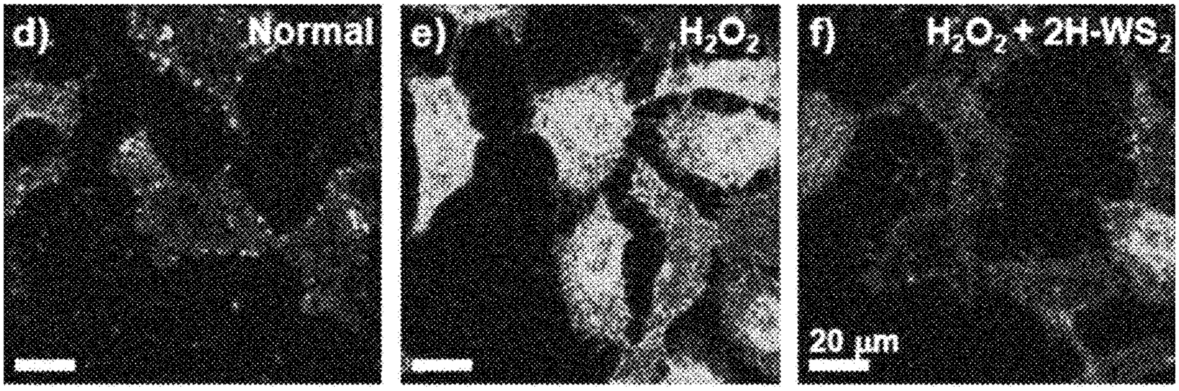
FIG. 12 is a fluorescence image of normal HaCaT keratinocyte apoptosis, hydrogen peroxide-stimulated HaCaT keratinocyte apoptosis, and 2H-$WS_2$ keratinocyte apoptosis treated with hydrogen peroxide stimulation and HaCaT nanosheets, respectively, from the left.

FIG. 12 shows fluorescence images of normal HaCaT keratinocytes, hydrogen peroxide-stimulated HaCaT keratinocytes, hydrogen peroxide-stimulated HaCaT keratinocytes, and 2H-$WS_2$ keratinocytes treated with hydrogen peroxide stimulation and nanosheets, respectively, from the left, and these were stained with Annexin V-FITC.

Referring to FIG. 12, the cells killed by hydrogen peroxide are clearly seen (middle picture), but the number of killed cells is reduced in the right picture, similar to the left picture of normal cells, as treated with 2H-$WS_2$. This is a sufficient description of the treating burns effect of the 2H-$WS_2$ according to the present invention, and is consistent with the oxidation stress suppressing effect of FIG. 11.

Figure 13:
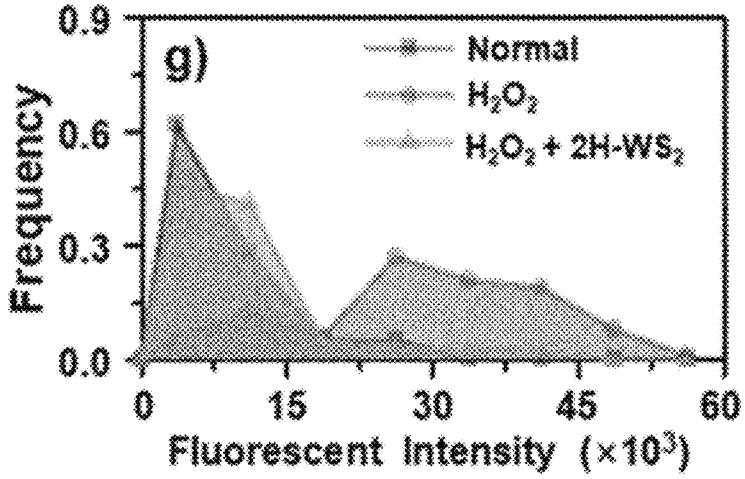
FIG. 13 is a result of quantitative apoptosis of FIG. 12.

FIG. 13 shows the results of quantitative apoptosis of normal hydrogen peroxide-stimulated HaCaT keratinocytes, based on FIG. 12.

Referring to FIG. 13, when 2H-$WS_2$ and hydrogen peroxide were treated, apoptosis was similar to that of normal cells (Normal, gray region) (see green region).

Figure 14:
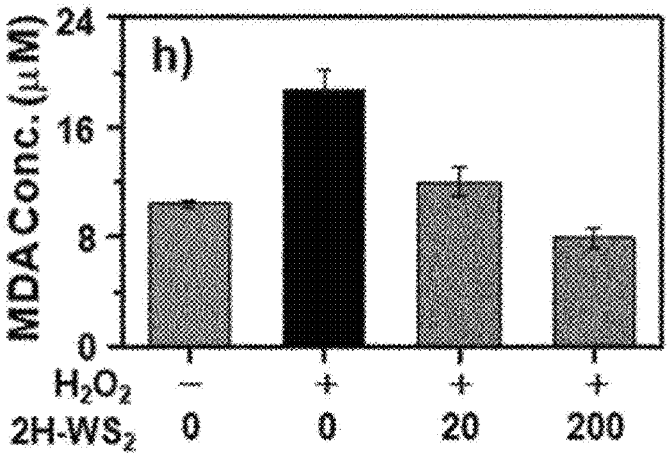
FIG. 14 shows results of showing lipid peroxidation levels of HaCaT keratinocytes after treatment according to hydrogen peroxide or hydrogen peroxide and 2H-$WS_2$ nanosheet concentration.

FIG. 14 shows results of showing lipid peroxidation levels of HaCaT keratinocytes after treatment with different concentrations of hydrogen peroxide or hydrogen peroxide and 2H-$WS_2$ nanosheets.

Referring to FIG. 14, it may be seen that the level of lipid peroxidation decreases as the 2H-$WS_2$ concentration in the X-axis increases.

Figure 15:
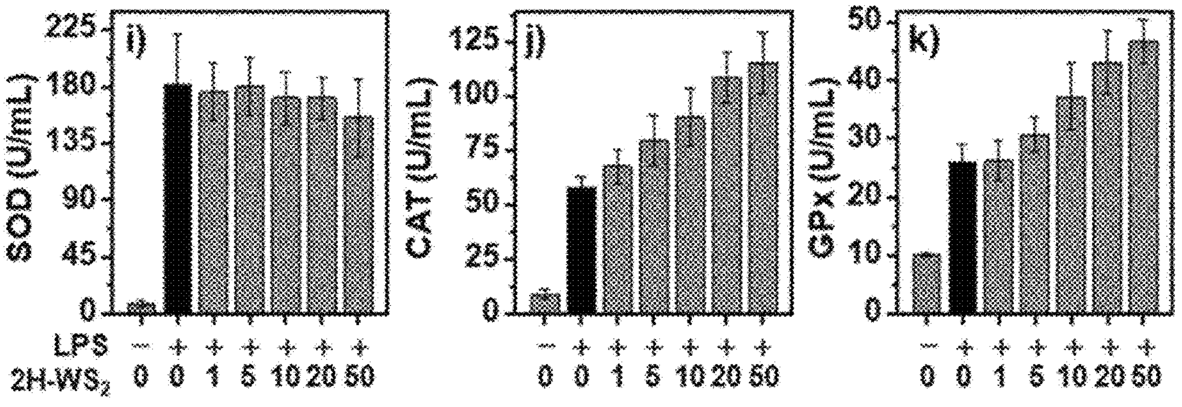
FIG. 15 shows the results of SOD, CAT and GPx expression levels of LPS-stimulated HaCaT keratinocytes after treatment with 2H-$WS_2$ nanosheets at various concentrations from the left.

FIG. 15 shows the results of SOD, CAT and GPx expression levels of LPS-stimulated HaCaT keratinocytes after treatment with 2H-$WS_2$ nanosheets at various concentrations from the left. Here, "+" and "−" indicate cases in which 2H-$WS_2$ treatment or no treatment is performed, and the lower values indicate treatment concentration (μM).

Referring to FIG. 15, SOD is not greatly changed according to 2H-$WS_2$ treatment, but particularly, CAT and GPx increase in proportion to the treatment concentration. Therefore, in this experiment, it can be confirmed that the 2H-$WS_2$ nanosheet according to the present invention increases the secretion amount of antioxidant enzyme in skin keratinocytes.

Figure 16:
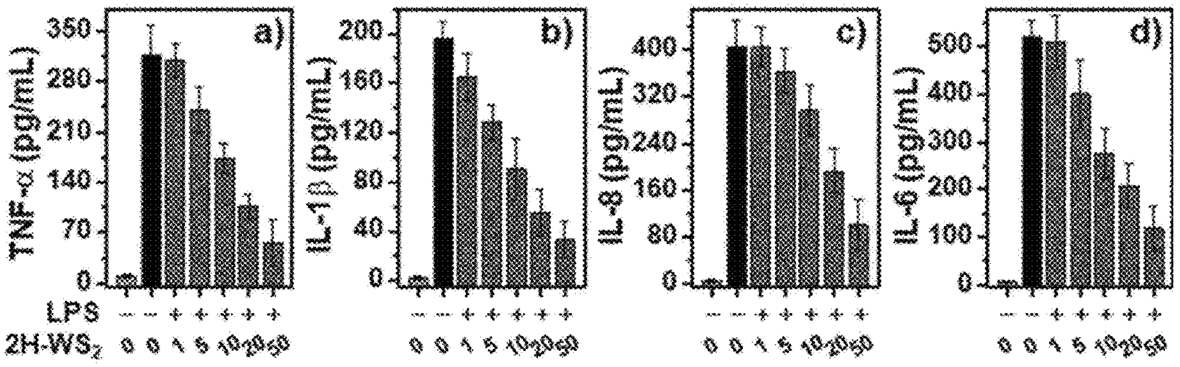
FIG. 16 shows the results of confirming the decrease in inflammatory cytokine secretion by 2H-$WS_2$ treatment in LPS-induced inflammatory HaCaT keratinocytes through LPS stimulation.

FIG. 16 shows the results of confirming the decrease in inflammatory cytokine secretion by 2H-$WS_2$ treatment in LPS-induced inflammatory HaCaT keratinocytes through LPS stimulation. In FIG. 16, the cytokines from the left are TNF-α, ILF-1β, IL-8 and IL-6, respectively.

Referring to FIG. 16, it may be confirmed that the secretion amount of inflammatory cytokine by the 2H-$WS_2$ nanosheet is reduced.

Figure 17:
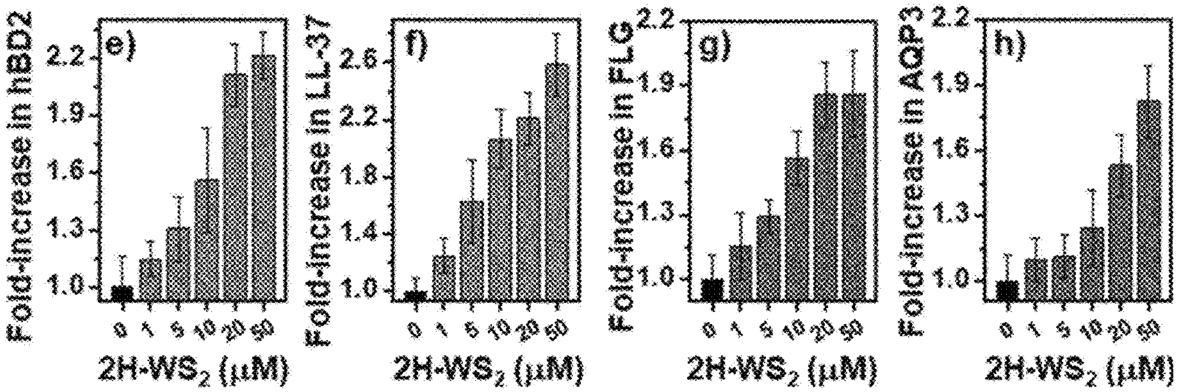
FIG. 17 shows the results of confirming an increase in secretion of the antibacterial peptide when 2H-$WS_2$ nanosheets are treated to skin keratinocytes.

FIG. 17 shows the results of confirming an increase in secretion of the antibacterial peptide when 2H-$WS_2$ nanosheets are treated to skin keratinocytes.

Referring to FIG. 17, cell peptides exhibiting antibacterial effects when 2H-$WS_2$ nanosheets are treated to the skin keratinocytes are increased. This proves that the 2H-$WS_2$ according to the present invention has an antibacterial effect as well as an anti-inflammatory effect.

Figure 18:
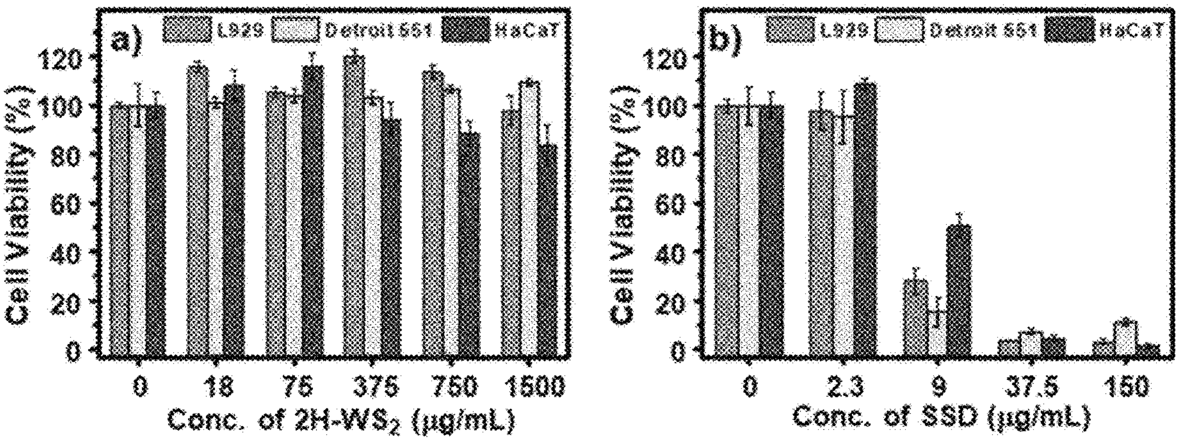
FIG. 18 shows the results of toxicity tests of 2H-$WS_2$ nanosheets for various skin cells and the existing commercial therapeutic agent, silver sulfadiazine (SSD), from the left.

FIG. 18 shows the results of toxicity tests of 2H-$WS_2$ nanosheets for various skin cells and the existing commercial therapeutic agent, silver sulfadiazine (SSD), from the left.

Referring to FIG. 18, the 2H-$WS_2$ nanosheet according to the present invention has little toxicity to normal skin cells compared to the existing drug, SSD. This confirms that the TMD-based burn treatment agent according to the present invention is an alternative which can effectively solve the problem such as death of normal cells of the existing burn treatment agent.

In-Vivo Animal Testing

Figure 19:
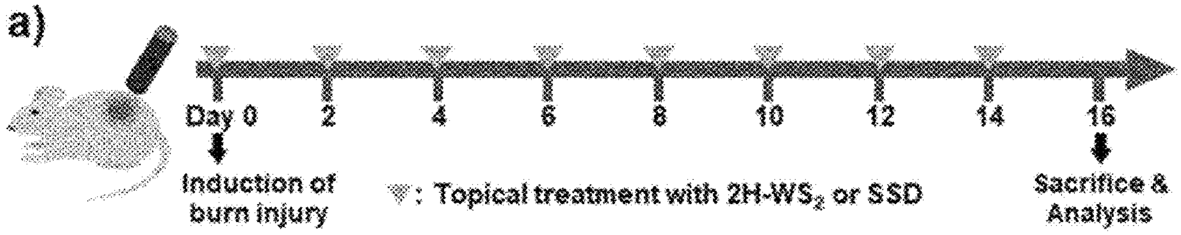
FIG. 19 is a schematic diagram of an animal experiment performed in the present experimental example.

FIG. 19 is a schematic diagram of an animal experiment performed in the present experimental example.

Referring to FIG. 19, in the present experiment, after causing the burn on the 0th day, the 2H-$WS_2$ of Example and the SSD of Comparative Example were treated at 2-day intervals, and the tissue analysis was performed on the 16th day. The following experimental data were obtained on the 16th day after treating the image tissue of each component.

Figure 20:
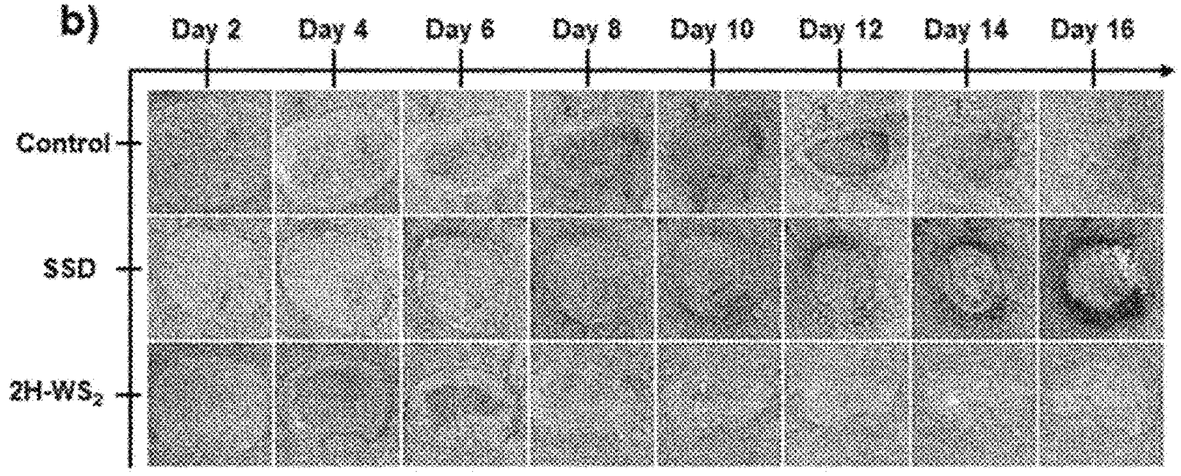
FIG. 20 is a picture of wound tissue treated with SSD or 2H-$WS_2$ nanosheets over time, with untreated (control, Control).

FIG. 20 is a picture of wound tissue treated with SSD or 2H-$WS_2$ nanosheets over time, with untreated (Control group).

Referring to FIG. 20, when the image is treated with the SSD, the surrounding normal tissue turns black due to the toxicity of the normal cells. In contrast, TMD-based burn treatment agent (2H-$WS_2$) according to the present invention normally treats burns without such side effects as SSD.

Figure 21:
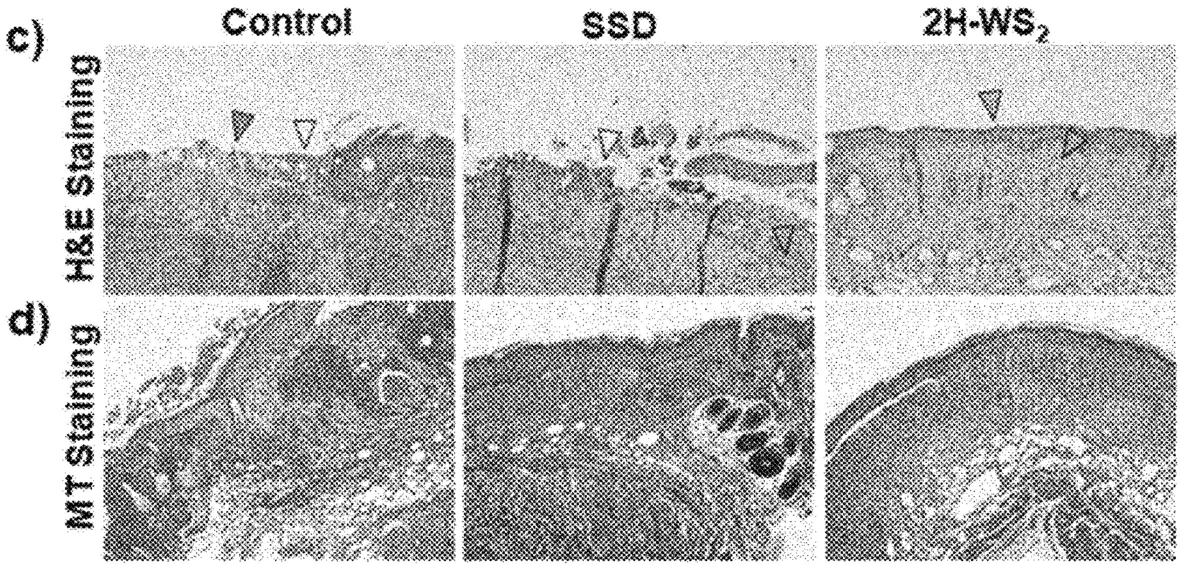
FIG. 21 is a tissue picture with H&E staining (top) and MT staining (bottom).

FIG. 21 is a tissue picture with H&E staining (top) and MT staining (bottom). In FIG. 21, a red arrow indicates epidermis exposed without re-epithelialization, a yellow arrow indicates an inflammatory exudate, a green arrow indicates an epidermis exposed with local epidermis regeneration, and a blue arrow indicates fibroblasts.

Referring to FIG. 21, TMD-based burn treatment agent (2H-$WS_2$) according to the present invention recovers to the epidermis, which is the same experimental result as the analysis result of FIG. 22 below.

Figure 22:
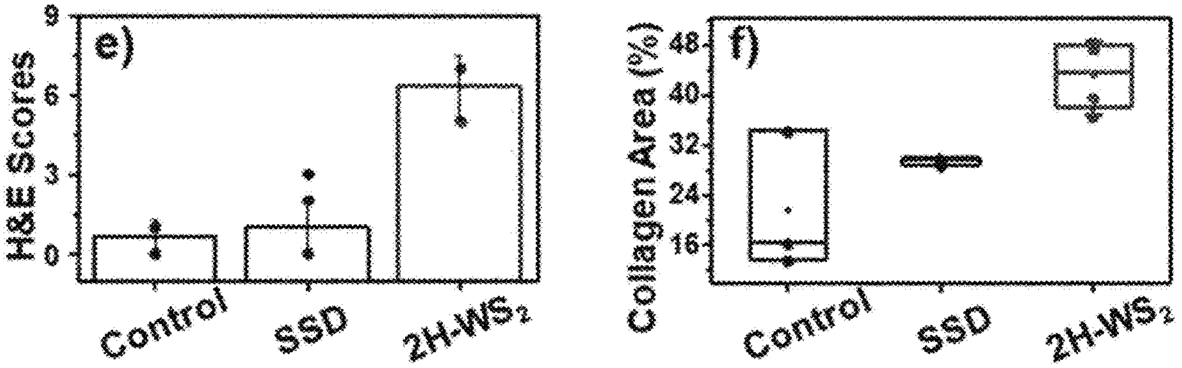
FIG. 22 shows the results of analyzing the histopathological score (H&E Score) and collagen area of tissue on day 16 treated with control group untreated (Control, control group), Example 2H-$WS_2$, and Comparative SSD.

FIG. 22 shows the results of analyzing the histopathological score (H&E Score) and collagen area of tissue on day 16 treated with control group untreated (Control group), Example 2H-$WS_2$, and Comparative SSD.

Referring to FIG. 22, histopathological score and collagen area increase compared to the untreated case, and significantly increase compared to the existing commercial drug SSD.

Figure 23:
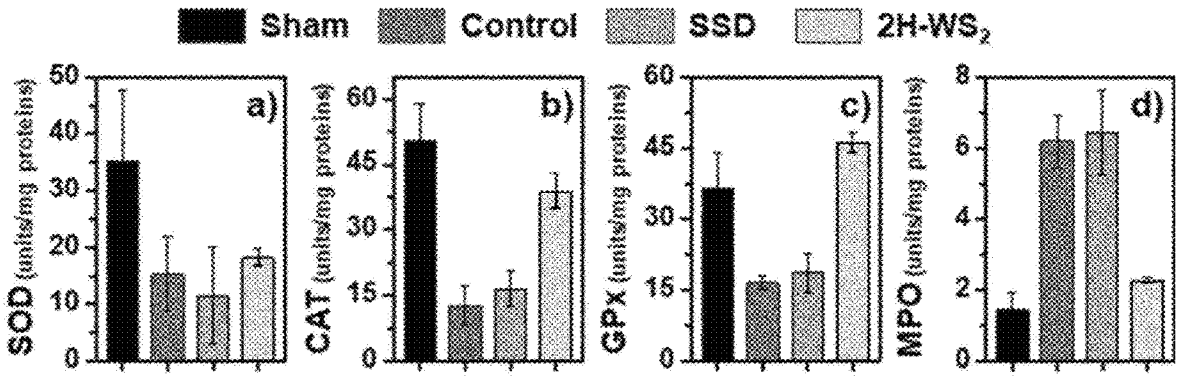
FIG. 23 shows the results of analyzing the expression levels of antioxidant enzymes (SOD, CAT, and GPx) and oxidase (MPO) in the image tissue of mice when the mice are treated with no burn injury (Sham), when the mice are not treated with Control (control group), and when the mice are treated with SSD or 2H-$WS_2$ nanosheets.

FIG. 23 shows the results of analyzing the expression levels of antioxidant enzymes (SOD, CAT, and GPx) and oxidase (MPO) in the image tissue of mice when the image injury is normal (Sham), when the image injury is absent (control group, Control), and when the SSD or 2H-$WS_2$ nanosheet is treated.

Referring to FIG. 23, the treatment with 2H-$WS_2$, which is the material according to the embodiment of the present invention, shows an excellent effect compared to the SSD, which is the material of the control group or the comparative example.

Figure 24:
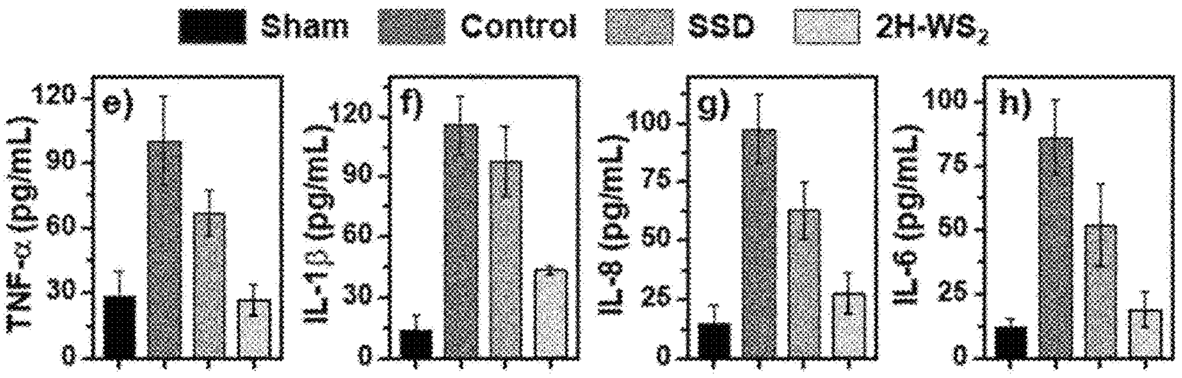
FIG. 24 shows the results of analyzing the expression levels of inflammatory cytokines (TNF-α, IL-1β, IL-8, and IL-6) in the image tissues of mice when normal (Sham), untreated (control group, Control), and treated with SSD or 2H-$WS_2$ nanosheets from the left.

FIG. 24 shows the results of analyzing the expression levels of inflammatory cytokines (TNF-$\alpha$, IL-1$\beta$, IL-8, and IL-6) in the image tissues of mice when normal (Sham), untreated (control group, Control), and treated with SSD or 2H-$WS_2$ nanosheets, respectively, from the left.

Referring to FIG. 24, the amount of cytokines is remarkably reduced according to the use of the TMD-based materials according to the present invention.

Figure 25:
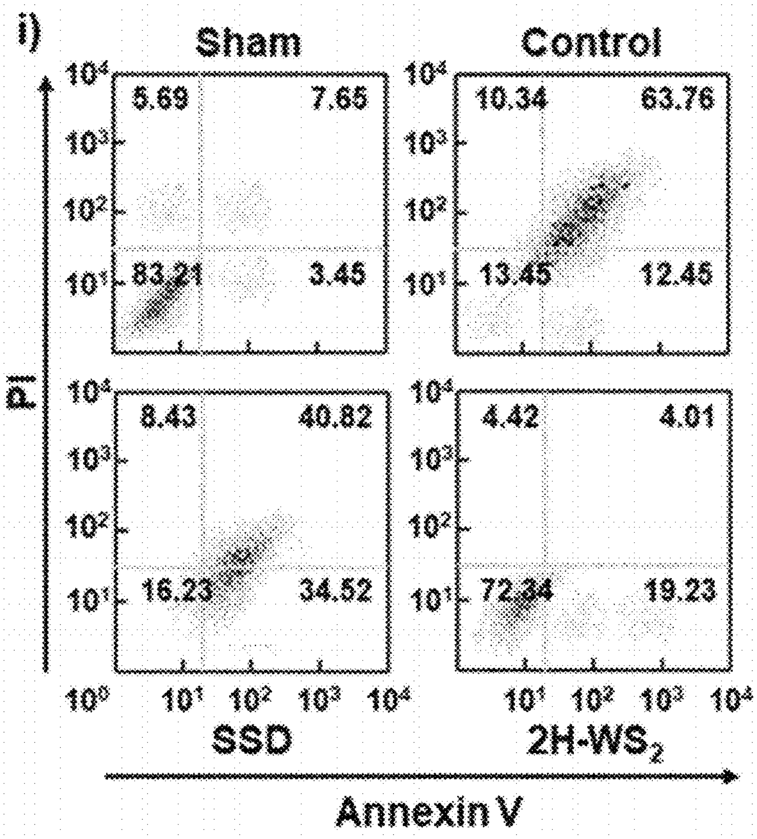
FIG. 25 is a representative flow cytometry plot of apoptosis levels in burn tissue for normal (Sham), untreated (control, Control), SSD or 2H-$WS_2$ nanosheet treatment with no burn wounds.

FIG. 25 is a representative flow cytometry plot of the death levels in the imaging tissues of mice when normal (Sham), untreated (Control group), and treated with SSD or 2H-$WS_2$ nanosheets.

Referring to FIG. 25, when the 2H-$WS_2$ nanosheet was treated, apoptosis values similar to those of normal cells were observed, and results were superior to those of SSD, which is a control or a comparative material.

Figure 26:
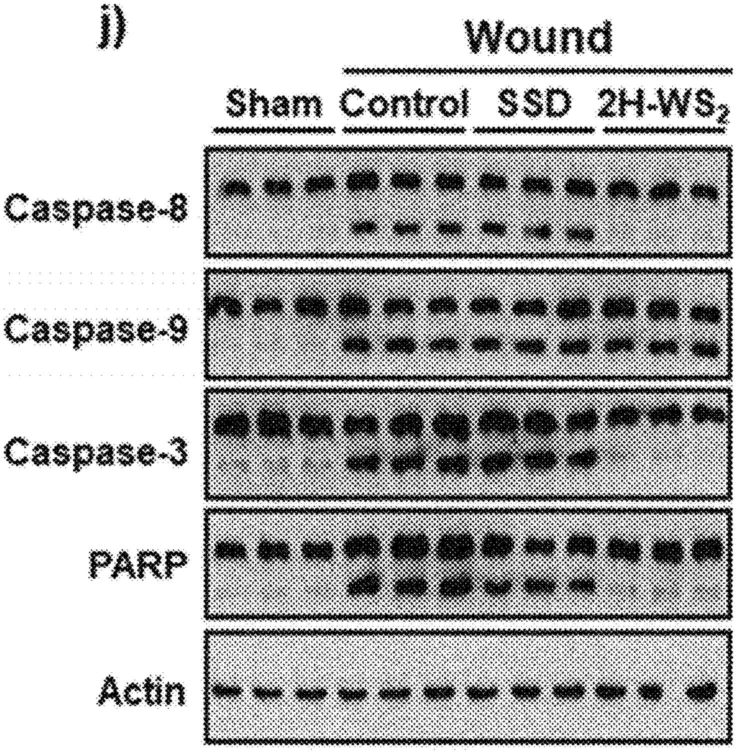
FIG. 26 shows western blot results of caspase-8, caspase-9, caspase-3 and PARP in rat imaging tissues when normal (Sham), untreated (control, Control), SSD or 2H-$WS_2$ nanosheet treatment without imaging wounds.

FIG. 26 shows western blot results of caspase-8, caspase-9, caspase-3 and PARP in rat imaging tissues when normal (Sham), untreated (Control), SSD or 2H-$WS_2$ nanosheet treatment without imaging wounds.

Referring to FIG. 26, western blot results having the same or similar pattern as that of Sham can be confirmed, and this confirms that the image therapeutic agent according to the present invention has low toxicity and anti-apoptotic effect for normal cells, anti-inflammatory effect based on high active oxygen species/nitrogen species scavenging activity, and specific anti-bacterial effect through expression of an anti-bacterial peptide.

Figure 27:
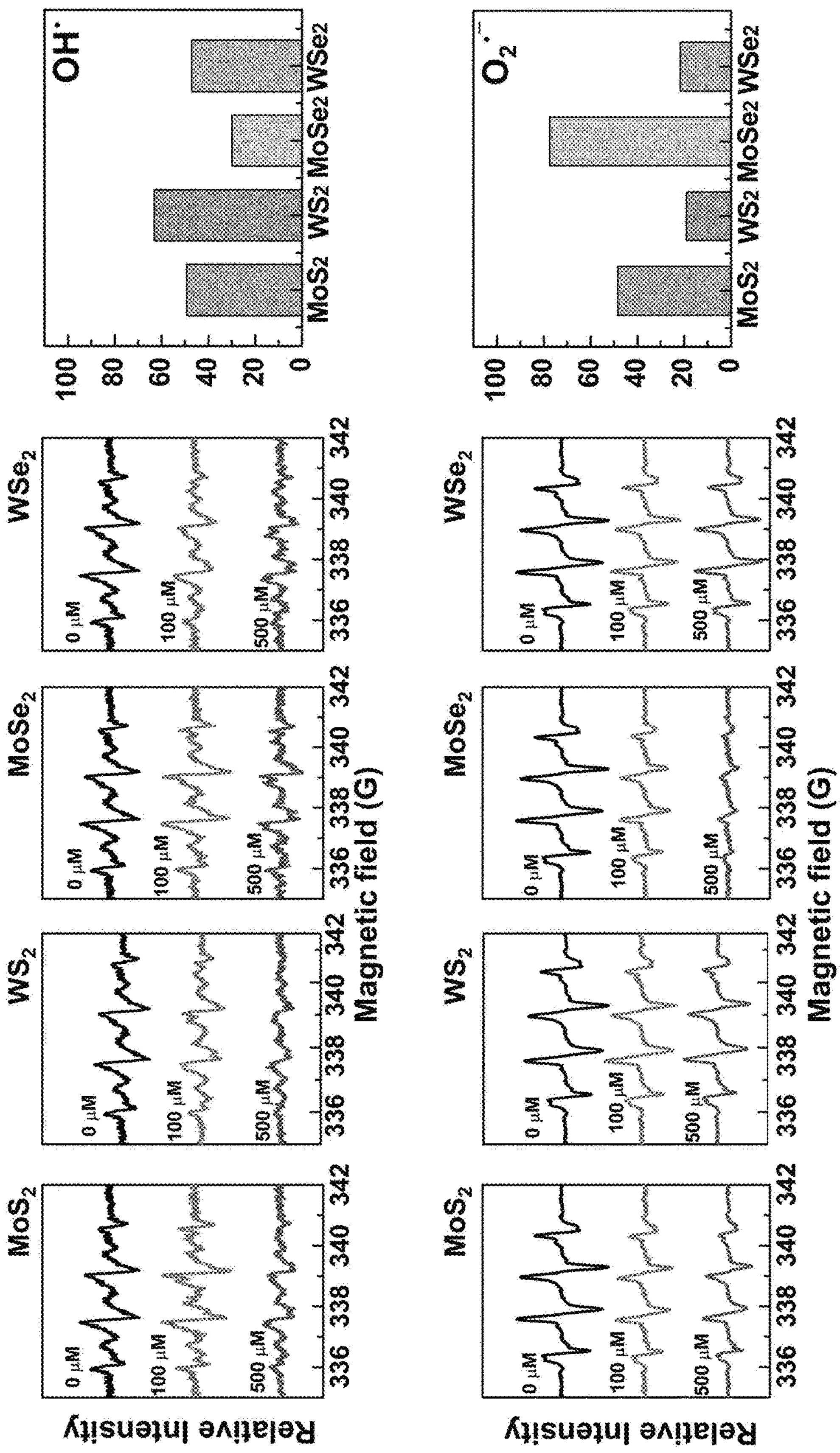
FIGS. 27 to 29 show the results of testing the active oxygen and active nitrogen scavenging activities of four types of TMD including $WS_2$.
Figure 28:
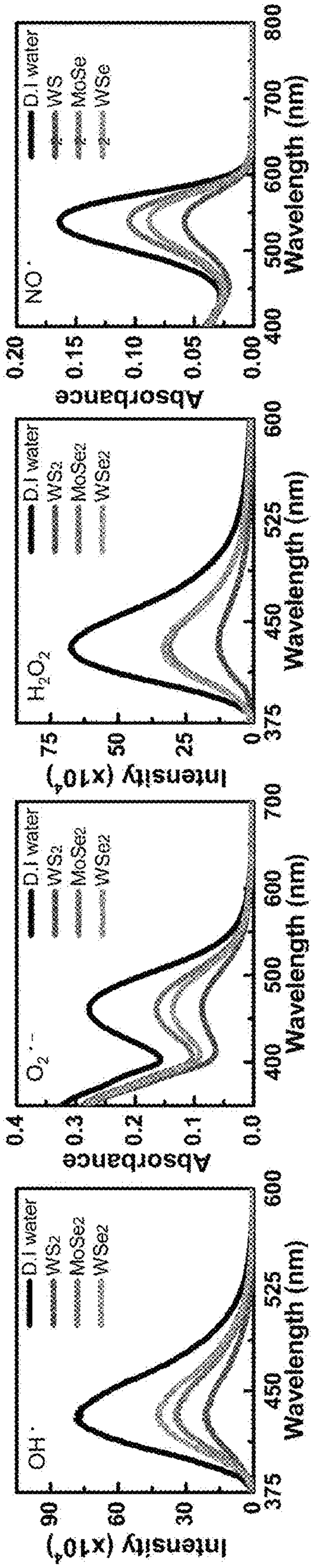
Figure 29:
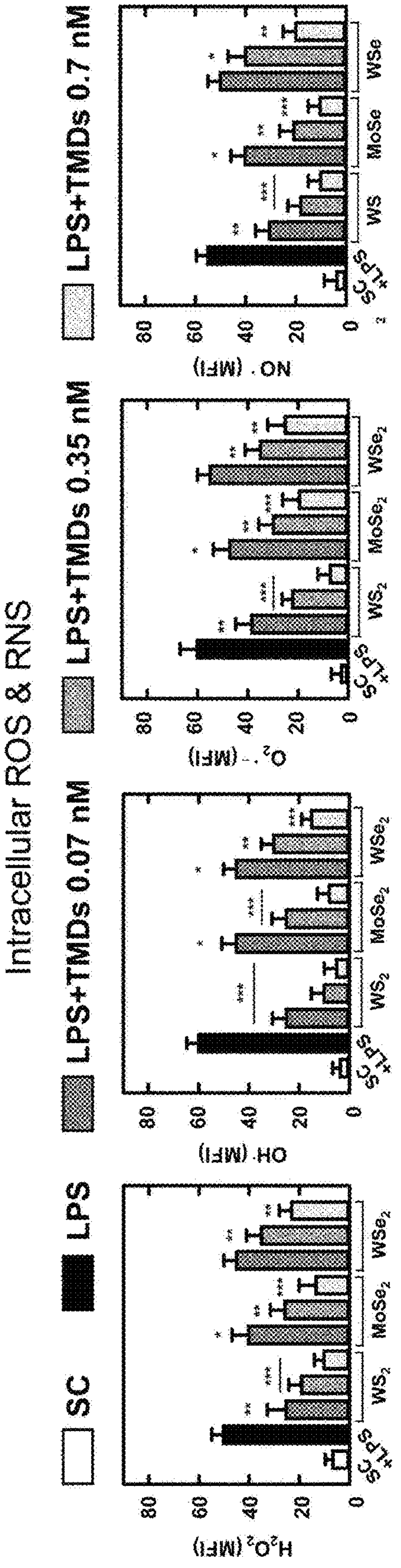

FIGS. 27 to 29 show the results of testing the active oxygen and active nitrogen scavenging activities of four types of TMD including $WS_2$.

Referring to FIGS. 27 and 28, $WS_2$ has the highest active oxygen and active nitrogen scavenging ability, and $MoS_2$, $MoSe_2$, and $WSe_2$ all have excellent active oxygen scavenging ability. In addition, referring to FIG. 29, it can be confirmed that all of $WS_2$, $MoSe_2$, and $WSe_2$ have concentration-dependent active oxygen and active nitrogen scavenging ability. The above results demonstrate that TMD nanosheets selected from the group consisting of $WS_2$, $MoS_2$, $MoSe_2$, and $WSe_2$ have an anti-inflammatory effect based on active oxygen species/nitrogen species scavenging activity, and thus can be used as an active ingredient of a burn treatment agent.

Figure 30:
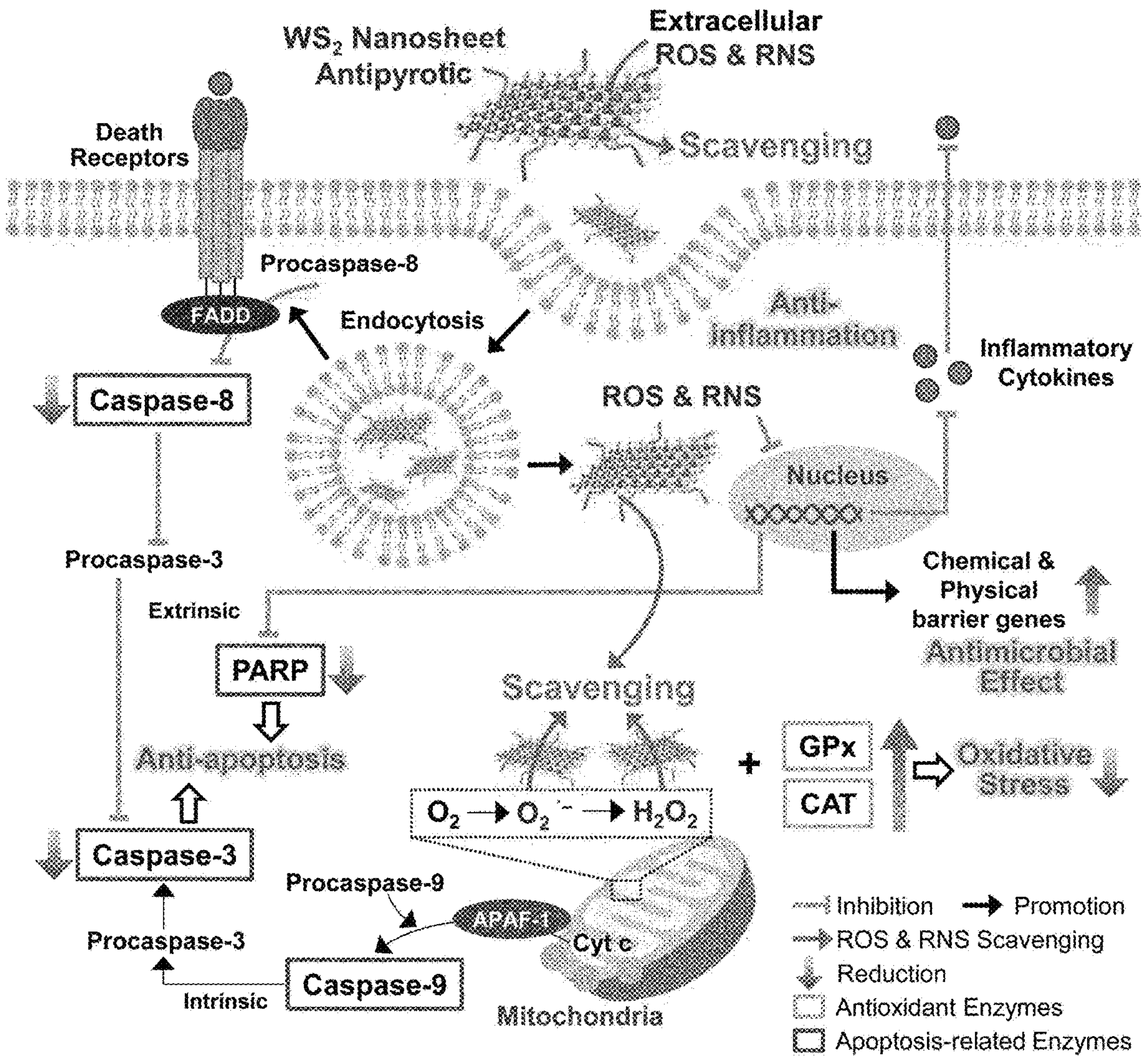
FIG. 30 is a schematic diagram of the mechanisms of the anti-inflammatory effect, the effect of preventing apoptosis due to external factors, and the antibacterial effect of 2H-$WS_2$ nanosheets.

FIG. 30 is a schematic diagram of the mechanisms of the anti-inflammatory effect, the effect of preventing apoptosis due to external factors, and the antibacterial effect of 2H-$WS_2$ nanosheets.

Referring to FIG. 30, mechanisms for anti-oxidation-based apoptosis prevention effect, anti-inflammatory effect, and specific anti-bacterial effect through expression of an anti-bacterial peptide of the 2H-$WS_2$ nanosheet may be confirmed.

The invention claimed is:

1. A pharmaceutical composition for treating burns comprising 2H-phase tungsten disulfide (2H-$WS_2$) nanosheets as an active ingredient, wherein the 2H-$WS_2$ has a trigonal prismatic crystal structure, and the composition provides burn healing efficacy while exhibiting reduced cytotoxicity against normal skin cells.

2. The pharmaceutical composition for treating burns of claim 1, wherein the 2H-$WS_2$ is in the form of nanosheets having an average lateral size of 50-200 nm.

3. The pharmaceutical composition for treating burns of claim 2, wherein the nanosheets are exfoliated via ultrasonication.

4. The pharmaceutical composition for treating burns of claim 3, wherein the nanosheets are displayed in a poly(ε-caprolactone)-block-poly(ethylene glycol) (PCL-b-PEG) solution.

5. The pharmaceutical composition for treating burns of claim 4, wherein the composition exhibits an absorption peak in a wavelength range of 600 to 700 nm.

6. The pharmaceutical composition for treating burns of claim 1, wherein the composition reduces apoptosis and expresses antimicrobial peptides while exhibiting anti-inflammatory activity.

7. The pharmaceutical composition for treating burns of claim 1, wherein the composition enhances antioxidant enzyme activity including catalase (CAT) and glutathione peroxidase (GPx).

8. A method for preparing pharmaceutical composition for treating burns, the method comprising: adding 2H-$WS_2$ to a PCL-b-PEG polymer solution; ultrasonically treating the added solution; and obtaining a composition from a supernatant of the ultrasonically treated solution.

9. The method for preparing pharmaceutical composition for treating burns of claim 8, wherein the 2H-$WS_2$ nanosheets have a trigonal prismatic phase.

10. The method for preparing pharmaceutical composition for treating burns of claim 8, wherein the composition is the pharmaceutical composition for treating burns of claim 1.

11. The method for preparing pharmaceutical composition for treating burns of claim 8, wherein the composition is the pharmaceutical composition for treating burns of claim 2.

12. The method for preparing pharmaceutical composition for treating burns of claim 8, wherein the composition is the pharmaceutical composition for treating burns of claim 3.

13. The method for preparing pharmaceutical composition for treating burns of claim 8, wherein the composition is the pharmaceutical composition for treating burns of claim 4.

14. The method for preparing pharmaceutical composition for treating burns of claim 8, wherein the composition is the pharmaceutical composition for treating burns of claim 5.

15. The method for preparing pharmaceutical composition for treating burns of claim 8, wherein the composition is the pharmaceutical composition for treating burns of claim 6.

16. The method for preparing pharmaceutical composition for treating burns of claim 8, wherein the composition is the pharmaceutical composition for treating burns of claim 7.

* * * * *